US00PP17567P2

(12) United States Plant Patent
Grueber

(10) Patent No.: US PP17,567 P2
(45) Date of Patent: Apr. 3, 2007

(54) ***EURPHORBIA* PLANT NAMED 'INNEUPHDIA'**

(50) Latin Name: *Eurphorbia hypericifolia*
Varietal Denomination: Inneuphdia

(75) Inventor: Garry Grueber, Mainz (DE)

(73) Assignee: InnovaPlant GmbH & Co. KG, Gensingen (DE)

( * ) Notice: Subject to any disclaimer, the term of this patent is extended or adjusted under 35 U.S.C. 154(b) by 0 days.

(21) Appl. No.: 11/236,712

(22) Filed: Sep. 27, 2005

(51) Int. Cl.
*A01H 5/00* (2006.01)

(52) U.S. Cl. ..... Plt./302
(58) Field of Classification Search ..... Plt./302
See application file for complete search history.

*Primary Examiner*—Kent Bell
*Assistant Examiner*—Annette H Para
(74) *Attorney, Agent, or Firm*—C. A. Whealy

(57) ABSTRACT

A new and distinct cultivar of *Euphorbia* plant named 'Inneuphdia', characterized by its compact, upright and outwardly spreading plant habit; freely branching habit; freely flowering habit; and white-colored flower bracts.

1 Drawing Sheet

Botanical designation: *Euphorbia hypericifolia.*
Cultivar denomination: 'Inneuphdia'.

BACKGROUND OF THE INVENTION

The present Invention relates to a new and distinct cultivar of *Euphorbia* plant, botanically known as *Euphorbia hypericifolia,* and hereinafter referred to by the cultivar name Inneuphdia.

The new *Euphorbia* is a naturally-occurring whole plant mutation of an unnamed selection of *Euphorbia hypericifolia,* not patented. The new *Euphorbia* was discovered and selected from within a population of plants of the unnamed selection in a controlled environment in Gensingen, Germany in the spring of 2004.

Asexual reproduction of the new cultivar by terminal vegetative cuttings since the summer of 2004 in Gensingen, Germany has shown that the unique features of this new *Euphorbia* are stable and reproduced true to type in successive generations.

SUMMARY OF THE INVENTION

Plants of the cultivar Inneuphdia have not been observed under all possible environmental conditions. The phenotype may vary somewhat with variations in environment such as temperature, light intensity and daylength without, however, any variance in genotype.

The following traits have been repeatedly observed and are determined to be the unique characteristics of 'Inneuphdia'. These characteristics in combination distinguish 'Inneuphdia' as a new and distinct cultivar:

1. Compact, upright and outwardly spreading plant habit.
2. Freely branching habit.
3. Freely flowering habit.
4. White-colored flower bracts.

In side-by-side comparisons conducted in Gensingen, Germany, plants of the new *Euphorbia* differed from plants of the parent selection in the following characteristics:

1. Plants of the new *Euphorbia* were more uniform than plants of the parent selection.

2. Plants of the new *Euphorbia* were more freely branching than plants of the parent selection.
3. Plants of the new *Euphorbia* were more freely flowering than plants of the parent selection.
4. Plants of the new *Euphorbia* had smaller flowers than plants of the parent selection.

Plants of the new *Euphorbia* can be compared to plants of the *Euphorbia* cultivar Imprefant, disclosed in U.S. Plant Pat. No. 16,908. In side-by-side comparisons conducted in Gensingen, Germany, plants of the new *Euphorbia* differed from plants of the cultivar Imprefant in the following characteristics:

1. Plants of the new *Euphorbia* had green-colored leaves whereas plants of the cultivar Imprefant had burgundy-colored leaves.
2. Plants of the new *Euphorbia* were more freely flowering than plants of the cultivar Imprefant.

BRIEF DESCRIPTION OF THE PHOTOGRAPHS

The accompanying colored photographs illustrate the overall appearance of the new cultivar, showing the colors as true as it is reasonably possible to obtain in colored reproductions of this type. Colors in the photographs may differ slightly from the color values cited in the detailed botanical description which accurately describe the colors of the new *Euphorbia.*

The photograph at the top of the sheet is a close-up view of typical flowers of 'Inneuphdia'.

The photograph at that bottom of the sheet comprises a side perspective view of a typical plant of 'Inneuphdia' grown in a container.

DETAILED BOTANICAL DESCRIPTION

The aforementioned photographs and following observations and measurements describe plants grown in Bonsall, Calif., in a polyethylene-covered greenhouse during the spring and summer with day temperatures ranging from 10° C. to 32° C. and night temperatures ranging from 2° to 21°

C. After planting rooted cuttings, plants were grown for about 18 with one plant per 12.5-cm container. Plants were pinched one time. Color references are made to The Royal Horticultural Society Colour Chart, 1995 Edition, except where general terms of ordinary dictionary significance are used.

Botanical classification: *Euphorbia hypericifolia* cultivar Inneuphdia.

Parentage: Naturally-occurring branch whole plant mutation of an unnamed selection of *Euphorbia hypericifolia,* not patented.

Propagation:

*Type.*—By cuttings.

*Time to initiate roots, summer.*—About 14 days at 20° C.

*Time to initiate roots, winter.*—About 18 days at 20° C.

*Time to develop roots.*—About 20 days at temperatures of 20° C.

*Root description.*—Fine, white in color.

*Rooting habit.*—Freely branching.

Plant description:

*Plant form and growth habit.*—Compact and mounded plant habit; plants upright to outwardly spreading; inverted triangle; perennial subshrub. Moderate growth rate.

*Branching habit.*—Freely branching, usually about four primary branches each with numerous secondary and tertiary lateral branches developing per plant; open plant form.

*Plant height.*—About 18 cm.

*Plant diameter.*—About 42 cm.

*Lateral branch description.*—Length: About 14 cm. Diameter: About 3 mm. Internode length: About 2.8 cm. Strength: Strong. Texture: Smooth, glabrous. Color: 146A.

Foilage description:

*Arrangement.*—Opposite; simple.

*Length.*—About 3.1 cm.

*Width.*—About 1.5 cm.

*Shape.*—Elliptical.

*Apex.*—Acute.

*Base.*—Attenuate to acute.

*Margin.*—Entire.

*Texture, upper and lower surfaces.*—Pubescent.

*Venation.*—Pinnate, arcuate.

*Color.*—Developing foliage, upper surface: 146A. Developing foliage, lower surface: 146B. Fully developed foliage, upper surface: 147A. Mature foliage, lower surface: 147B. Venation, upper surface: 147A. Venation, lower surface: 147C.

*Petiole.*—Length: About 3 cm. Diameter: Less than 1 mm. Texture, upper and lower surfaces: Sparsely pubescent. Color, upper and lower surfaces: 146A.

Inflorescence description:

*Natural flowering season.*—Spring to summer in Southern California; flowering continuous during this period.

*Flower arrangement.*—Single rotate flowers arranged in umbel-like compound terminal cymes. Very freely flowering with about 500 flower buds and flowers per plant. Flowers face upright and outwardly. Flowers persistent. Flowers not fragrant.

*Inflorescence height.*—About 1.5 cm.

*Inflorescence diameter.*—About 2.4 cm.

*Flower diameter.*—About 5 mm.

*Flower depth* (*height*).—About 7 mm.

*Flower longevity on the plant.*—About ten days.

*Floral bracts.*—Quantity/arrangement: Two; opposite. Length: About 8 mm. Width: About 2 to 3 mm. Shape: Elliptical to lanceolate. Apex: Rounded to acute. Base: Fused. Margin: Entire. Texture, upper and lower surfaces: Glabrous; smooth. Color: When opening and fully expanded, upper surface: 155D. When opening and fully opened, lower surface: 155D.

*Peduncles.*—Length: About 5 cm to 5.5 cm. Diameter: About 1 mm. Strength: Strong. Angle: About 60° to 90° from vertical. Texture: Smooth, glabrous. Color: 146A.

*Pedicels.*—Length: About 4 mm. Diameter: Less than 1 mm. Strength: Strong. Angle: About 45° from vertical. Texture: Smooth, glabrous. Color: 146B.

*Cyathia.*—Length: About 7 mm. Diameter: About 5 mm. Shape: Oval; eight terminal points. Aspect: Upright. Color: 145A.

*Nectaries.*—Quantity per flower: About four. Shape: Lunate. Length: About 2 mm. Width: About 3 mm. Color: 146A; towards the apices, 155D.

*Reproductive organs.*—Androecium: Quantity: About four stamens per cyathia. Shape: Oval, bi-lobed. Length: Less than 1 mm. Color: 158C. Pollen: Scarce. Pollen color: 158D. Gynoecium: Quantity: One per cyathia. Pistil length: About 3 mm. Style length: Less than 1 mm. Style color: 155D. Stigma shape: Six-parted. Stigma color: 155D. Ovary color: 146A.

*Fruit/seed.*—Fruit and seed production has not been observed.

Disease/pest resistance: Plants of the new *Euphorbia* have been observed to be resistant to Powdery Mildew. Plants of the new *Euphorbia* not been observed to be resistant to pests and other pathogens common to *Euphorbia.*

Temperature tolerance: Plants of the new *Euphorbia* are tolerant to temperatures as low as 10° C. and as high as 40° C.

It is claimed:

1. A new and distinct *Euphorbia* plant named 'Inneuphdia', as illustrated and described.

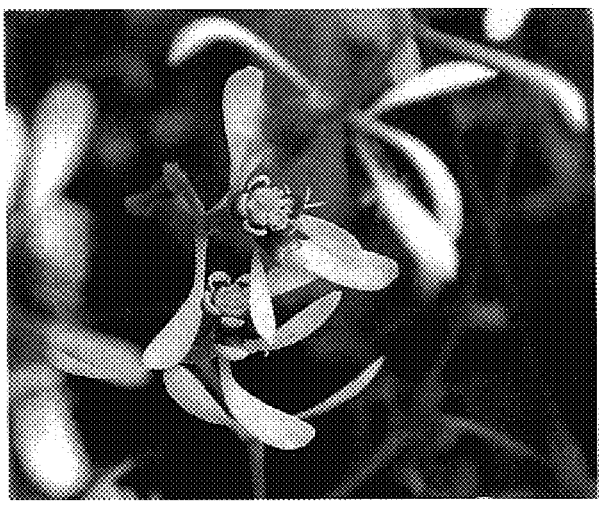
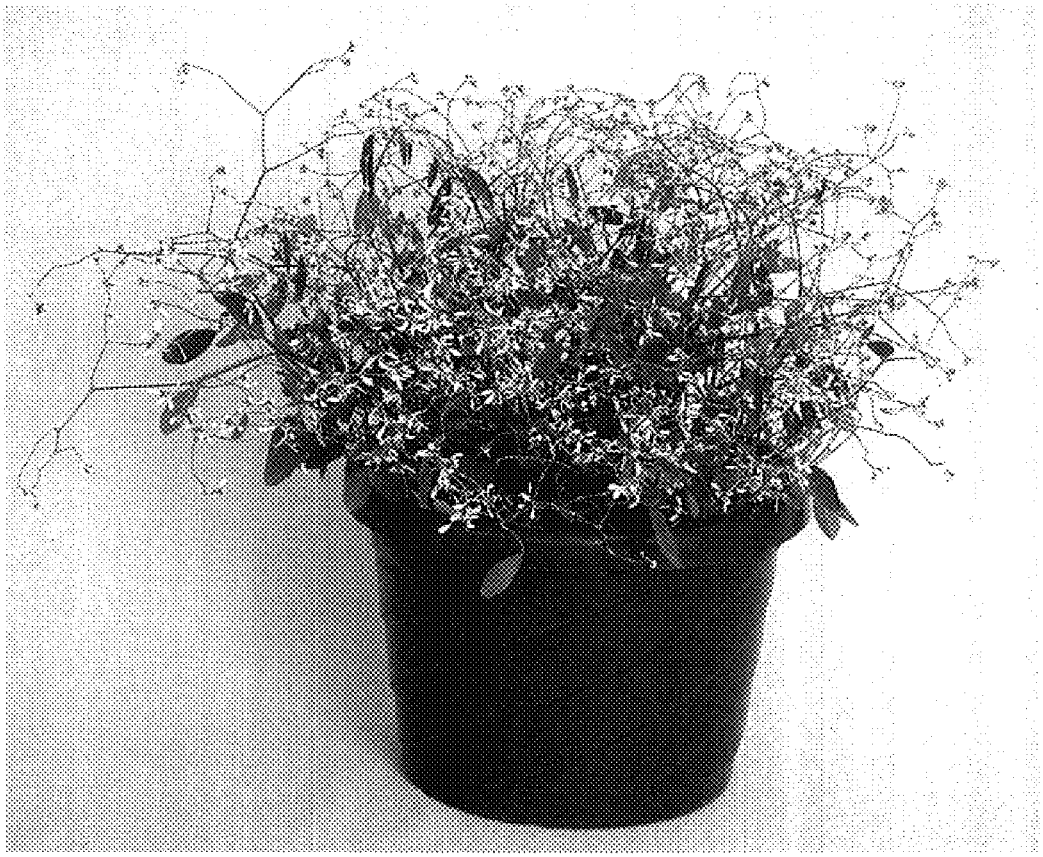

* * * * *